United States Patent
Kato et al.

(10) Patent No.: US 12,220,471 B2
(45) Date of Patent: Feb. 11, 2025

(54) AQUEOUS LIQUID COSMETIC

(71) Applicant: JO Cosmetics Co., Ltd., Tokyo (JP)

(72) Inventors: Shogo Kato, Tokyo (JP); Kazumi Kondo, Tokyo (JP)

(73) Assignee: JO Cosmetics Co., Ltd., Tokyo (JP)

( * ) Notice: Subject to any disclaimer, the term of this patent is extended or adjusted under 35 U.S.C. 154(b) by 563 days.

(21) Appl. No.: 17/610,734

(22) PCT Filed: May 8, 2020

(86) PCT No.: PCT/JP2020/018603
§ 371 (c)(1),
(2) Date: Nov. 12, 2021

(87) PCT Pub. No.: WO2020/230706
PCT Pub. Date: Nov. 19, 2020

(65) Prior Publication Data
US 2022/0218575 A1  Jul. 14, 2022

(30) Foreign Application Priority Data

May 14, 2019 (JP) .................. 2019-091151

(51) Int. Cl.
| | |
|---|---|
| A61K 8/26 | (2006.01) |
| A61K 8/02 | (2006.01) |
| A61K 8/06 | (2006.01) |
| A61K 8/25 | (2006.01) |
| A61K 8/362 | (2006.01) |
| A61K 8/81 | (2006.01) |
| A61Q 1/10 | (2006.01) |

(52) U.S. Cl.
CPC ............. *A61K 8/26* (2013.01); *A61K 8/0254* (2013.01); *A61K 8/062* (2013.01); *A61K 8/25* (2013.01); *A61K 8/362* (2013.01); *A61K 8/8152* (2013.01); *A61Q 1/10* (2013.01); *A61K 2800/43* (2013.01); *A61K 2800/621* (2013.01); *A61K 2800/651* (2013.01)

(58) Field of Classification Search
None
See application file for complete search history.

(56) References Cited

U.S. PATENT DOCUMENTS

| | | | |
|---|---|---|---|
| 10,391,042 B2 | 8/2019 | Lingoes et al. | |
| 2002/0051756 A1 | 5/2002 | Sato | |
| 2005/0129637 A1 * | 6/2005 | Aota | A61Q 1/10 424/63 |
| 2009/0175813 A1 | 7/2009 | Morita et al. | |
| 2010/0104610 A1 * | 4/2010 | Dueva-Koganov | A61K 8/817 424/70.6 |
| 2010/0180796 A1 | 7/2010 | Kitamura et al. | |
| 2013/0101538 A1 | 4/2013 | Nagasaka et al. | |
| 2015/0216771 A1 * | 8/2015 | Sakuma | A61Q 1/10 424/401 |
| 2018/0369081 A1 * | 12/2018 | Sakuma | A45D 34/04 |
| 2020/0131374 A1 | 4/2020 | Hayashi et al. | |
| 2021/0189143 A1 | 6/2021 | Hayashi et al. | |

FOREIGN PATENT DOCUMENTS

| | | | | |
|---|---|---|---|---|
| CN | 101355923 B | * | 11/2012 | ............. A61K 8/11 |
| CN | 102985056 A | | 3/2013 | |
| JP | 2004175709 A | * | 6/2004 | |
| JP | 2007153744 A | | 6/2007 | |
| JP | 4036560 B2 | | 1/2008 | |
| JP | 2015151374 A | * | 8/2015 | |
| JP | 2016041674 A | | 3/2016 | |
| JP | 2016079147 A | * | 5/2016 | |
| JP | 2018172617 A | * | 11/2018 | ............. B22F 1/14 |
| WO | 2007123115 A1 | | 11/2007 | |

OTHER PUBLICATIONS

English translation of Abstract for CN102985056A, Mar. 20, 2013.
English Abstract for JP2016041674A, Mar. 31, 2016.
English Abstract for JP2000247833 A, Sep. 12, 2000.
English Abstract for JP2007153744 A, Jun. 21, 2007.
English Abstract for JP2016079147 A, May 16, 2016.
English Abstract for JP2018172617 A, Nov. 8, 2018.

* cited by examiner

*Primary Examiner* — Melissa S Mercier
*Assistant Examiner* — Caralynne E Helm
(74) *Attorney, Agent, or Firm* — CAHN & SAMUELS, LLP

(57) ABSTRACT

An aqueous liquid cosmetic containing 1 to 20% by mass of (A) a flake aluminum powder coated with a layer containing a silicon compound; 0.5 to 10% by mass of (B) a polycarboxylic acid-based dispersant having a mass-average molecular weight of 10,000 or less; and 1 to 40% by mass of (C) a film-forming polymer emulsion in terms of a solid content is provide. Normally, the aqueous liquid cosmetic contains at least 40% by mass of water, and further may optionally contain (D) a color pigment as another ingredient. This aqueous liquid cosmetic is suitable for eye makeup applications such as eyeliners, eyebrows, eye colors, and the like.

7 Claims, No Drawings

AQUEOUS LIQUID COSMETIC

This application is a U.S. national stage application of PCT/JP2020/018603 filed on 8 May 2020 and claims priority to Japanese patent document 2019-091151 filed on 14 May 2019, the entireties of which are incorporated herein by reference.

TECHNOLOGICAL FIELD

The present invention relates to an aqueous liquid cosmetic, and more specifically to an aqueous liquid cosmetic which is excellent in brightness, color development and rub resistance and suitable for an eye makeup cosmetic.

BACKGROUND TECHNOLOGY

As a cosmetic to be applied around the eye such as an eyeliner, an eyebrow, an eye color, and the like, various types of cosmetics such as an oil-based, a water-based, and the like are known. Hereinafter, the cosmetic is sometimes referred to as an eye makeup cosmetic. Among these cosmetics, the water-based cosmetic is excellent in making a cosmetic coating having less smudge and is also excellent in ease of removing the coating. Hence, in recent years, the water-based cosmetic has been intensively developed. The eye makeup cosmetic is used to enhance impression of the eye. As the eye makeup cosmetic, black one having a great effect of making the eyes look bigger has been used for a long time. However, in recent years, uses of the eye makeup cosmetic have diversified, and there is a tendency to formulate a highly glittering pearl pigment or lame agent to satisfy a demand for higher fashionability.

As such an aqueous liquid cosmetic, for example, patent document 1 proposes a liquid cosmetic containing a mica-based pearl pigment and an anionic polymer such as xanthan gum as a dispersant for the pigment. As to a pearl pigment, there is a problem that it tends to sediment early because of having a larger particle size as compared with usual organic or inorganic pigments, further, once sedimentated it tends to form a hard cake because of its flat particle shape, which is difficult to be re-dispersed. The cosmetic described in the literature solves such a drawback of the mica-based pearl pigment by formulating an anionic polymer as a dispersant. The literature, in its examples, discloses aqueous cosmetics containing black iron oxide-coated (titanium dioxide-coated mica) or iron oxide-coated (titanium dioxide-coated mica) as the pearl pigment, and xanthan gum, tragacanth gum and alkyl acrylate copolymer emulsion as the dispersant (see Table 1).

Patent document 2 proposes an aqueous eyeliner composition containing a glittering pigment, carbon black, a polysaccharide derived from a microorganism, a volatile alcohol, and an alkyl acrylate copolymer emulsion. The literature discloses that the composition is excellent in rub resistance, color development and smoothness of writing, and is also excellent in storage stability. It also discloses that a colorant-coated (titanium dioxide-coated mica) such as iron oxides-coated (titanium dioxide-coated mica) and carmine-coated (titanium dioxide-coated mica) is preferable as the glittering pigment (see paragraph 0015), and that sufficient performance cannot be obtained when no polysaccharide derived from a microorganism is included (see Comparative Example 2 in Table 1).

In addition, patent document 3 proposes an aqueous liquid makeup cosmetic containing a plate-like pigment, a pigment dispersant, a film-forming agent, a surfactant, and a spherical powder. The literature discloses that the cosmetic has a relaxed sedimentation of the plate-like pigment, and that even when the plate-like pigment sediments during storage, the plate-like pigment sedimented can be re-dispersed (see paragraph 0011). This literature discloses that the plate-like pigment is a pearl pigment specific examples of which include mica, titanium dioxide-coated mica and the like (see paragraph 0015), and that the pigment dispersant is a homopolymer or copolymer of monomers selected from acrylic acid, methacrylic acid or their ($C_1$-$C_4$ or $C_8$) alkyl esters specific examples of which include a copolymer of t-butyl acrylate, ethyl acrylate and methacrylic acid, and examples of commercial products of the copolymer include Luvimer 100P available from BASF (see paragraph 0020).

On the other hand, an aluminum-based powder composed of aluminum or an aluminum alloy, or a powder containing the aluminum-based powder as an ingredient is conventionally known in the art of paints and cosmetics as a glittering color material with unique metallic luster. For example, patent document 2 mentions an aluminum powder, an iron oxides-coated aluminum powder and a powder of laminated film composed of polyethylene, aluminum, and epoxy resin as a specific example of the glittering pigment (see paragraph 0014) and discloses examples in which the powder of polyethylene/aluminum/epoxy laminated film is used with a (titanium dioxide-coated mica)-based glittering pigment (see Examples 2 and 4 of Table 1). In addition, patent document 3 discloses an aluminum-coated polyester film and an aluminum powder pigment as well as mica and titanium dioxide-coated mica as an example of the plate-like pigment (see claim 2). However, the literature discloses no pigments containing aluminum as a specific example of the pearl pigment (see paragraph 0015). Further, it is silent about what kind of performance is exhibited when pearl pigments containing aluminum are formulated in an aqueous liquid cosmetic.

PRIOR ART DOCUMENT

Patent Document

Patent Document 1: JP-A-2000-247833
Patent Document 2: JP-A 2007-153744
Patent Document 3: Republished WO 2007/123115

DISCLOSURE OF THE INVENTION

Problem to be Solved by the Invention

The present invention was completed under the aforementioned background art, and an object of the present invention is provide an aqueous liquid cosmetic which is excellent in brightness, color development, and rub resistance, and is also excellent in storage stability.

Means Used to Solve the Problem

As a result of intensive studies to solve the above problem, the present inventors found that when a specific flaky aluminum, a polycarboxylic acid-based dispersant having a specific molecular weight and a film-forming polymer emulsion are used in combination, an aqueous liquid cosmetic which provides a cosmetic coating film excellent in brightness, color development, and rub resistance, and is also excellent in storage stability can be obtained. The present invention was completed based on the above knowledge.

Thus, the present invention provides an aqueous liquid cosmetic containing 1 to 15% by mass of (A) a flaky aluminum powder coated with a silicon compound-containing layer, 0.5 to 10% by mass of (B) a polycarboxylic acid-based dispersant having a mass-average molecular weight of 10,000 or less, and 1 to 40% by mass of (C) a film-forming polymer emulsion in terms of a solid content.

Effect of the Invention

The aqueous liquid cosmetic of the present invention is excellent in brightness, color development and rub resistance, and also is excellent in storage stability.

Embodiment for Carrying Out the Invention

In the aqueous liquid cosmetic of the present invention, the flaky aluminum powder coated with a silicon compound-containing layer used as the component (A) is a composite powder having one or more coating layers on a surface of a flaky aluminum powder. At least one layer of the coating layer is a silicon compound-containing layer. Here, the term "aluminum powder" in the present invention includes a powder of an alloy containing aluminum as a main component, for example, an alloy containing aluminum as a main component and 20% by mass or less, particularly 10% by mass or less of at least one metal selected from silicon, magnesium, manganese, copper, zinc, nickel, vanadium, lead, antimony, tin, cadmium, bismuth, titanium, chromium, and iron. Specifically, an aluminum alloy having good corrosion resistance may be selected among those described in Japanese Industrial Standards (JIS H 4140).

When the coating layer is composed of one layer, the coating layer is a silicon compound-containing layer, and in case that the coating layer is composed of two or more layers, at least one of the layers is composed of a silicon compound-containing layer. Examples of the other coating layer include a layer of a metal oxide such as titanium dioxide, zirconium dioxide and iron oxides, a molybdenum-containing coating, a phosphoric acid compound coating, and the like The flaky aluminum powder to be a substrate of the composite powder can be obtained by grinding a piece of aluminum according to conventional methods. Specifically, a stamp method using a stamp mill, a ball mill method or the like can be used. The flaky aluminum powder has preferably an average particle diameter of 1 to 300 μm, more preferably 5 to 100 μm on its major axis. When the average particle diameter is less than 1 μm, brightness tends to low. When the average particle diameter is more than 300 μm, rough feel is likely to occur. An aspect ratio (major axis/thickness) of the flaky aluminum powder is preferably 2 to 1,000, more preferably 10 to 500. If the aspect ratio is too small, brightness of the powder tends to low. When it is too large, it becomes difficult to uniformly disperse the powder.

The silicon compound-containing layer to be at least one layer of the coating layer is preferably a layer composed of a compound containing an Si—O bond. Hereinafter, this layer is also referred to "Si—O-based coating layer." Examples of such a layer include a layer containing at least one compound selected from silane-based compounds and silicon oxides. That is, there are mentioned a layer containing a silane-based compound $[H_3SiO(H_2SiO)_nSiH_3]$ (where n is any positive integer) and a layer containing a silicon oxide such as $SiO_2$ and $SiO_2 \cdot nH_2O$ (where n is any positive integer). These silicon compound may be either crystalline or amorphous. Preferably, it is amorphous. Thus, a layer containing an amorphous silica is preferably used as the layer containing a silicon oxide such as silica.

Also, a layer formed by using an organosilicon compound as a starting material can be used as the Si—O-based coating layer. The organosilicon compound may be a silane coupling agent. Thus, the silicon compound-containing layer may contain an organosilicon compound, or a component derived therefrom within a range where the effects of the present invention are essentially not impaired. The silicon compound-containing layer need not be a coating layer composed of only a silicon compound, and may include additives other than the silicon compound, impurities, and the like in a range that the properties of the present invention are essentially not impaired.

A content of the silicon compound-containing layer in the component (A) is preferably 5% by mass or more, more preferably 20% by mass or more in view of stability of the aluminum powder in the aqueous liquid cosmetic. When the content is excessively small, an aqueous liquid cosmetic tends to cause a loss of gloss over time, or the aluminum component tends to react with water to generate hydrogen gas.

The flaky aluminum powder coated with the silicon compound-containing layer can be prepared according to known methods such as that described in JP-A 2018-172617. For example, after dispersing the flaky aluminum in isopropanol, a first coating layer is formed with a metal molybdenum powder and then a silicon-containing compound layer is formed as a second layer using tetraethoxysilane to form a composite powder that is composed of a flaky aluminum, a metal molybdenum layer, and a silicon-containing compound layer. Examples of commercial products of such a flaky aluminum powder include Cosmicolor Celest Frost Silver (manufactured by Toyo Aluminum K.K.)

A content of the flaky aluminum powder coated with the silicon compound-containing layer being the component (A) is 1 to 20% by mass, preferably 2 to 15% by mass, more preferably 3 to 10% by mass based on the whole amount of the cosmetic. When the content is below 1% by mass, brightness becomes low, and when more than 20% by mass, rub resistance becomes low.

(B) Polycarboxylic Acid-Based Dispersant

In the present invention, a polycarboxylic acid-based dispersant having a mass-average molecular weight of 10,000 or less is used in order to improve dispersibility of the flaky aluminum powder being the component (A). The polycarboxylic acid-based dispersant is water-soluble, and its use suppresses sedimentation of the flaky aluminum powder and facilitates re-dispersion of the flaky aluminum powder sedimented even when the flaky aluminum powder sediments.

In the present invention, the polycarboxylic acid-based dispersant means a dispersant containing, as an active ingredient, a water-soluble polymer having a polymerized unit of an ethylenically unsaturated carboxylic acid in its molecule, or a water-soluble salt of a polymer having a polymerized unit of an ethylenically unsaturated carboxylic acid in its molecule. Specific examples of the polycarboxylic acid include a homopolymer or copolymer of a lower ethylenically unsaturated fatty acid monomer such as acrylic acid, methacrylic acid, maleic acid, itaconic acid, and a copolymer of the lower ethylenically unsaturated fatty acid monomer and an unsaturated olefin such as ethylene, propylene, butene, pentene, hexene, and styrene. A type of the polycarboxylic acid salt is not particularly limited as long as it is acceptable as a cosmetic, and examples thereof include an alkali metal salt such as sodium salt and potassium salt, an ammonium salt and an organic amine salt. Of these, sodium salt or potassium salt is preferably used.

A mass-average molecular weight of the polycarboxylic acid-based dispersant is important to be 10,000 or less. It is preferably 9,000 to 500, more preferably 7,000 to 2,000. When the mass-average molecular weight exceeds 10,000, it becomes difficult to apply a cosmetic due to increased viscosity. The mass-average molecular weight of the polycarboxylic acid-based dispersant can be measured by gel permeation chromatography (GPC) using polyethylene glycol having a known molecular weight as a standard substance.

When the component (B) is a salt of polycarboxylic acid, it is usually prepared by neutralizing a polycarboxylic acid with a base in advance. Also, it may be formed in situ by adding a polycarboxylic acid and a base individually during a production process of a cosmetic.

Examples of the component (B) include Jurymer AC-10P (polyacrylic acid aqueous solution, average molecular weight: 9,000, solid content: 7% by mass), Jurymer AC-10SL (polyacrylic acid aqueous solution, average molecular weight: 3,000, solid content: 40%), Jurymer AC-103 (Sodium polyacryate aqueous solution, average molecular weight: 6,000, solid content: 40%) , Aron A-6001 (Carboxylic acid-based copolymer sodium salt aqueous solution, average molecular weight: 8,000, solid content: 40% (all of which are manufactured by Toagosei Co., Ltd.), Aquaric DL-40 (sodium polyacrylate aqueous solution, average molecular weight: 3,500, solid content: 40%), Aquaric YS-100 (Sodium polyacrylate aqueous solution, average molecular weight: 5, 500, solid content: 45%) (all of which are manufactured by Nippon Shokubai Co., Ltd.) and the like. Among them, an acrylic acid-based dispersant containing a polyacrylic acid or its salt as an active ingredient is preferably used.

A content of the component (B) is 0.5 to 10% by mass, preferably 0.5 to 7.5% by mass based on the total amount of the cosmetic in terms of a solid content. If the content of the component (B) is too small, re-dispersibility decreases. On the other hand, when the content is excessively large, it becomes difficult to apply a cosmetic due to increased viscosity.

In the present invention, a use ratio by mass of the component (A) to the component (B) [(A)/(B)] is 1/0.1 to 1/2, preferably 1/0.15 to 1/1.5, more preferably 1/0.2 to 1/1. If the ratio of the component (A) is excessively large, re-dispersibility decreases, and conversely, if too small, application becomes difficult.

(C) Film-Forming Polymer Emulsion

In the present invention, a film-forming polymer emulsion is used as the component (C). This is a water dispersion of a water insoluble polymer. Specific examples thereof include alkyl acrylate copolymer emulsion, alkyl methacrylate copolymer emulsion, styrene-alkyl acrylate copolymer emulsion, styrene-alkyl methacrylate copolymer emulsion, vinyl acetate polymer emulsion, vinylpyrrolidone-styrene copolymer emulsion, alkyl acrylate-vinyl acetate copolymer emulsion, alkyl methacrylate-vinyl acetate copolymer emulsion, acrylic acid-alkyl acrylate copolymer emulsion, acrylic acid-alkyl methacrylate copolymer emulsion, methacrylic acid-alkyl acrylate copolymer emulsion, methacrylic acid-alkyl methacrylate copolymer emulsion, and alkyl acrylate-dimethicone copolymer emulsion. The component (C) may be an emulsion of a composite polymer such as a core-shell polymer which is composed of a copolymer of an ethylenically unsaturated carboxylic acid monomer and a styrene monomer and at least one of the other polymer and/or copolymer.

Specific examples of the alkyl acrylate copolymer emulsion include acrylates/ethylhexyl acrylate copolymer (INCI name: ACRYLATES/ETHYLHEXYL ACRYLATE COPOLYMER). An example of commercially available products thereof is Daitosol 5000SJ (manufactured by Daito Kasei Kogyo Co., Ltd.). Specific examples of the styrene/alkyl acrylate copolymer emulsion include styrene/acrylates copolymer (INCI name; STYRENE/ACRYLATES COPOLYMER) which is also referred to ALKYL ACRYLATE/STYRENE COPOLYMER in the quasi-drug raw material specification 2006. Examples of commercially available products thereof include Yodosol GH-41F (manufactured by Akzo Nobel K.K.), Daitosol 5000STY (manufactured by Daito Kasei Kogyo Co., Ltd.), and the like.

Specific examples of the emulsion of composite polymer such as a core-shell polymer which is composed of a copolymer of an ethylenically unsaturated carboxylic acid monomer and a styrene monomer and the other polymer(s) and/or copolymer(s) include Emupoly CE-119N (manufactured by Gifu Shellac Manufacturing Co., Ltd.) which is an emulsion of a core-shell copolymer composed of acrylic acid-2-ethylhexyl acrylate copolymer and methacrylate-alpha-methylstyrene copolymer.

The film-forming polymer emulsion being the component (C) is usually an emulsion in which an resin component is finely dispersed in an aqueous component in a concentration of 20 to 60% by mass in terms of a solid content. A content thereof is 1 to 40% by mass based on the whole cosmetic in terms of a solid content, preferably 2 to 35% by mass, more preferably 3 to 30% by mass. If the content is too small, rub resistance decreases, and conversely, when excessively large, application of a cosmetic becomes difficult due to increased viscosity.

Since the aqueous liquid cosmetic of the present invention contains the components (A) to (C) described above in an aqueous medium, a large amount of water is contained in the whole cosmetic. A content of water can be suitably selected according to a desired formulation. Generally, it is 40% by mass or more, preferably 50 to 80% by mass.

(D) Color Pigment

The aqueous liquid cosmetic of the present invention may contain a color pigment as component (D). The color pigment may be any of an inorganic one and an organic one. It is not particularly limited by a shape, a particle diameter, or a particle structure as long it is generally used in the field of cosmetics.

Examples of the inorganic color pigment include inorganic white pigments such as titanium dioxide and zinc oxide; inorganic red pigment such as iron oxide, iron hydroxide and iron titanate; inorganic brown pigments such as gamma-iron oxide; inorganic yellow pigments such as yellow iron oxide and ochre; inorganic black pigments such as black iron oxide and carbon black; inorganic purple pigments such as manganese violet and cobalt violet; inorganic green pigments such as chromium hydroxide, chromium oxide, cobalt oxide and cobalt titanate; inorganic blue pigments such as Prussian blue and ultramarine; glittering color powders such as iron oxides-coated mica, iron oxides-coated (titanium dioxide-coated mica), organic pigmenttreated (titanium dioxide-coated mica), (titanium dioxide and iron oxides)-coated glass; and the like.

Examples of the organic color pigments include Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, and Blue No. 404; lakes formed by a metal such as zirconium, barium, and aluminum and a water soluble dye such as Red No. 3, Red No. 104, Red No. 106, Red No. 227, Red No. 230, Red No. 401, Red NO. 505, Orange No. 205, Yellow No. 4, Yellow No. 5, Yellow No. 202, Yellow No. 203, Green No. 3, and Blue No. 1; natural coloring materials such as chlorophyll, beta-carotene and their lakes; dyes and the like. These color pigments may be used alone or in combination of two or more.

A content of the color pigment in the aqueous liquid cosmetic can be selected as appropriate. The content is preferably 0.01 to 15% by weight, more preferably 0.05 to 10% by mass. When the content of the color pigment is excessively increased, rub resistance tends to reduce, and conversely, when the content is excessively small, coloring effect is apt to be insufficient.

In addition to the above components, the aqueous liquid cosmetic of the present invention may include components which are generally used in conventional cosmetics, for example, polyhydric alcohols, pigment dispersants, powders, pH adjusters, water-soluble thickeners, lower alcohols, oily components, ultraviolet absorbers, ultraviolet scattering agents, humectants, perfumes, antioxidants, preservatives, metal ion sequestering agents, defoamers, fibers, dyes, various extracts, and the like as long as the effects of the present invention are essentially not impaired.

The polyhydric alcohols to be used are not particularly limited as long as they are commonly used in cosmetics, and examples thereof include propylene glycol, dipropylene glycol, 1,3-butylene glycol, 1,2-pentylene glycol, 3-methyl-1,3-butanediol, polyethylene glycol, glycerin, diglycerin, and tetraglycerin. These polyhydric alcohols may be used alone or in combination of two or more. A content of the polyhydric alcohol is preferably 0.1 to 20% by mass, more preferably 1 to 15% by mass based on the total amount of the cosmetic. In case of including the polyhydric alcohol, antiseptic power is improved and when used in a pen-shaped container, drying of a tip and a brush tip can be reduced.

When a pigment other than the component (A) is included, a hydrophilic surfactant such as an anionic surfactant, a nonionic surfactant, a cationic surfactant, and an amphoteric surfactant can be used as a dispersant for the pigment. However, since a large amount of the hydrophilic surfactant impair water resistance of a cosmetic, a content of the hydrophilic surfactant is preferably 5% by mass or less, particularly 3% by mass or less relative to the total amount of the cosmetic.

Examples of the hydrophilic anionic surfactant include inorganic or organic salts of a fatty acid such as stearic acid and lauric acid, alkylbenzene sulfates, alkylsulfonates, alpha-olefin sulfonates, dialkyl sulfosuccinate, alpha-sulfonated fatty acid salts, acylmethyltaurine salts, N-methyl-N-alkyltaurine salts, polyoxyethylene alkyl ether sulfates, polyoxyethylene alkylphenyl ether sulfates, alkyl phosphates, polyoxyethylene alkyl ether phosphates, polyoxyethylene alkylphenyl ether phosphates, N-acylamino acid salts, N-acyl-N-alkylamino acid salts, alkylsulfosuccinic acid salts, polyaspartic acid salts, and the like. Of these, polyoxyethylene alkyl ether phosphates and polyaspartic acid salts are preferably used because of providing good pigment dispersibility.

Examples of the hydrophilic nonionic surfactant include glycerol fatty acid esters and alkylene glycol adducts thereof, polyglycerol fatty acid esters and alkylene glycol adducts thereof, propylene glycol fatty acid esters and alkylene glycol adducts thereof, sorbitan fatty acid esters and alkylene glycol adducts thereof, fatty acid esters of sorbitol and alkylene glycol adducts thereof, polyalkylene glycol fatty acid esters, sucrose fatty acid esters, and polyoxyalkylene alkyl ethers, glycerin alkyl ethers, polyoxyethylene alkylphenyl ethers, polyoxyethylene hydrogenated castor oils, alkylene glycol adducts of lanolin, polyoxyalkylene and alkyl-comodified organopolysiloxanes, polyether-modified organopolysiloxanes, and the like. Among these, polyoxyethylene alkyl ethers are preferably used because of providing good pigment dispersibility.

The powder is not particularly limited as long as it is commonly used in the field of cosmetics. For example, it may have a particle form such as a plate shape, a spindle shape, and a needle shape, and it may be porous or nonporous. Examples of the powder include inorganic powders, glittering powders, organic powders, and composite powders. More specifically, there are mentioned inorganic powders such as aluminum oxide, cerium oxide, silicic anhydride, magnesium oxide, zirconium oxide, magnesium carbonate, calcium carbonate, aluminum silicate, magnesium silicate, aluminum magnesium silicate, mica, synthetic mica, synthetic sericite, sericite, talc, kaolin, silicon carbide, barium sulfate, bentonite, smectite and boron nitride; glittering powders such as bismuth oxychloride, titanium dioxide-coated mica, silicic anhydride-coated (titanium dioxide-coated mica), titanium dioxide-coated glass powder and (titanium dioxide and silicic anhydride)-coated glass powder; organic powders such as magnesium stearate, zinc stearate, N-acyllysine and nylon; composite powders such as fine particle titanium dioxide-coated (titanium dioxide-coated mica), fine particle zinc oxide-coated (titanium dioxide-coated mica), barium sulfate-coated (titanium dioxide-coated mica), titanium dioxide-containing silica, zinc oxide-containing silica; polyethylene terephthalate-aluminum-epoxy laminated film powder, polyethylene terephthalate-polyolefin laminated film powder, polyethylene terephthalate-polymethyl methacrylate laminated film powder, and the like. These powders can be used alone or in combination of two or more.

Examples of the pH neutralizing agent include citric acid, ascorbic acid, sodium carbonate, and AMP. Examples of the preservative include phenoxyethanol, pentylene glycol and ethanol. Examples of the water-soluble thickener include hydroxyethyl cellulose and xanthan gum. A content of each ingredient added optionally is not particularly limited. It may be appropriately adjusted within a range where the effects of the present invention are essentially not impaired.

The aqueous liquid cosmetic of the present invention can be prepared according to conventional methods. For example, it can be prepared by mixing uniformly all ingredients for a cosmetic using a well-known agitation means such as a propeller type agitator. It can also be obtained by mixing the color pigment with a part of the aqueous ingredients and/or the pigment dispersant component in advance and then mixing them with the remaining ingredients.

The aqueous liquid cosmetic of the present invention can be suitably used as an eye cosmetic such as an eyeliner, an eyebrow and an eye color by appropriately adjusting a blending ratio of the above ingredients.

EXAMPLES

Hereinafter, the present invention will be described more specifically with reference to Examples and Comparative Examples, but the present invention is not limited by these examples. In the following description, an amount of each ingredient in the formulations is expressed in % by mass with respect to the whole composition unless otherwise indicated.

The evaluation methods of the aqueous liquid cosmetic in the following Examples and Comparative Examples are as follows.

Brightness and Color Development

A sample was filled into a dipping container with a brush tip mounted thereon, and then, using the brush tip, the sample was applied to a portion having a size of 2 cm×2.5 cm square on the backside of a black artificial skin (BIO-SKIN PLATE # BK manufactured by Beaulax Corporation) in amount of about 20 mg/cm$^2$ so as to leave no unapplied part. After drying the applied sample by allowing it to stand at room temperature for 3 hours, brightness and color development were evaluated.

Brightness-I (Visual Observation)

Ten evaluators visually observed the coating surface of the black artificial skin, and scored at four stages of 1 to 4 based on the evaluation criteria shown in (1) below. The total score of the ten evaluators was calculated to determine a degree of brightness based on the four-stage determination criteria shown in (2) below. In the determination criteria, A is the most excellent and D is the lowest.
(1) Evaluation Criteria
(Rating): (Evaluation)
    4: Feeling of strong brilliance
    3: Feeling of brilliance
    2: Feeling of slight brilliance
    1: Feeling of no brilliance
(2) Four-Stage Determination Criteria
(Determination): (Total of Evaluation Score)
    A: Total point is 14 or more
    B: Total point is 10 or more and less than 14
    C: Total point is 6 or more and less than 10
    D: Total point is less than 6
Brightness-II (Equipment Measurement):

Using a gloss meter (Glossy Meter GL200 manufactured by Courage+Khazaka electronic), an intensity of light was measured at an incidence angle of 60° and a light-receiving angle of 60° with respect to a surface of sample. This intensity of light is referred to Intensity A. An intensity of light which is referred to Intensity B was measured under the same conditions for a black specular glass having a refractive index of 1.567. A degree of gloss was calculated according to the following formula (1):

$$\text{Degree of gloss} = \text{Intensity } A / \text{Intensity } B \times 100 \quad (1)$$

Using a value of degree of gloss, the brightness-II was determined based on the following criteria.
(Determination): (Degree of Gloss)
    A: Degree of gloss is 28 or more
    B: Degree of gloss is 22 or more and less than 28
    C: Degree of gloss is 18 or more and less than 22
    D: Degree of gloss is less than 18
Color Development Using a color meter (Color and Whiteness Meter NW-12 manufactured by Nippon Denshoku Industries Co., Ltd.), colorimetry of the coating surface was performed to obtain Chroma C*. Using a value of Chroma C* obtained, a degree of color development was determined based on the following criteria. Chroma C* is defined in CIE 1976L*a*b* color system and is represented by $C^* = (a^{*2} + b^{*2})^{1/2}$.
(Determination): (Chroma C*)
    A: Chroma C* is 25 or more
    B: Chroma C* is 20 or more and less than 25
    C: Chroma C* is 10 or more and less than 20
    D: Chroma C* is less than 10
Rub Resistance A sample was filled in a dipping container with a brush tip mounted thereon, and then, a line having a width of 2 mm and a length of 20 mm was drawn on a black artificial skin (BIOSKIN PLATE # BK manufactured by Beaulax Corporation) using the brush tip. After drying the line for 3 hours, a finger covered by a finger cot was pressed lightly on the line and the line was rubbed 30 times back and forth. Then, by observing a state of the line after rubbing, rub resistance was determined based on the following criteria.
(Determination): (State of Line)
    A: No change is observed.
    B: A slight blur is observed in end portions of the line.
    C: A blur is observed in 20% or more of the line.
    D: A blur is observed in 50% or more of the line.
(Stability)

A sample was filled in a dipping container with a brush tip mounted thereon and stored in an incubator at 50° C. for 7 days. Then, the sample was coated on a piece of copy paper using the brush tip, and gloss was measured according to the above method. The result was compared with a gloss value of the sample prior to storage.
(Determination): (Gloss)
    A: No change
    B: Loss of gloss
(Re-Dispersibility)

Twenty grams of a sample was filled in a screw tube having a content of 30 mL and stored at room temperature for 7 days. Then, the screw tube was shaken up and down by hand to disperse a powder sedimented at the bottom of the screw tube, and the number of times of shaking necessary for re-disperse the powder was recorded. Re-dispersibility was determined by the following criteria.
(Determination): (State of Line)
    A: less than 10 times
    B: 10 times or more and less than 20 times
    C: 20 times or more and less than 30 times
    D: 30 times or more Examples 1 to 2 and Comparative Examples 1 to 5

<Eyeliner>

An eyeliner of the formulation shown in Table 1 was prepared according to the following production procedure and evaluated according to the methods described above as to brightness, color development, rub resistance, stability and re-dispersibility. The results are also shown in Table 1.
(Production Procedure)

(1) After dissolving the components 7 to 11 and 14 to 15 shown in Table 1 in purified water of the component 6, an interference pigment (any one of the components 1 to 5) and an inorganic pigment of the component 13 were added, and subsequently a resultant mixture was thoroughly stirred to prepare a water dispersion containing the interference pigment and the inorganic pigment.

(2) A polymer emulsion of the component 12 was added to the resulting water dispersion and mixed well to obtain an eyeliner.

TABLE 1

| | | Component | Example 1 | Example 2 | Comparative Example 1 | Comparative Example 2 | Comparative Example 3 | Comparative Example 4 | Comparative Example 5 |
|---|---|---|---|---|---|---|---|---|---|
| 1 | (A) | Silicon compound containing layer-coated aluminum powder ※1 | 4.00 | 8.00 | | | | | |
| 2 | | Flaky aluminum powder ※2 | | | | | | | 4.00 |
| 3 | | Titanium oxide-coated synthetic mica ※3 | | | 4.00 | 8.00 | | | |
| 4 | | Prussian blue-coated (titanium dioxide-coated mica) ※4 | | | | | 4.00 | | |
| 5 | | Titanium dioxide-coated plate like glass ※5 | | | | | | 4.00 | |
| 6 | | Purified water | Balance | Balance | Balance | Balance | Balance | Balance | Balance |
| 7 | | 1,2-Pentanediol | 3.00 | 3.00 | 3.00 | 3.00 | 3.00 | 3.00 | 3.00 |
| 8 | | 1,3-Butylene glycol | 5.00 | 5.00 | 5.00 | 5.00 | 5.00 | 5.00 | 5.00 |
| 9 | | Phenoxyethanol | 0.75 | 0.75 | 0.75 | 0.75 | 0.75 | 0.75 | 0.75 |
| 10 | | Hydroxyethyl cellulose | 0.30 | 0.30 | 0.30 | 0.30 | 0.30 | 0.30 | 0.30 |
| 11 | (B) | Soduim polyacrylate ※6 | 4.00 | 8.00 | 4.00 | 4.00 | 4.00 | 4.00 | 4.00 |
| 12 | (C) | (Acrylate/Ethylhexyl acrylate)copolymer ※7 | 25.00 | 25.00 | 25.00 | 25.00 | 25.00 | 25.00 | 25.00 |
| 13 | (D) | Prussian blue | 7.50 | 7.50 | 7.50 | 7.50 | 7.50 | 7.50 | 7.50 |
| 14 | | Sodium polyaspartate ※8 | 1.25 | 1.25 | 1.25 | 1.25 | 1.25 | 1.25 | 1.25 |
| 15 | | Aminomethylpropanol | Appropriate amount | Appropriate amount | Appropriate amount | Appropriate amount | Appropriate amount | Appropriate amount | Appropriate amount |
| | | Total | 100.00 | 100.00 | 100.00 | 100.00 | 100.00 | 100.00 | 100.00 |
| | | Component (A)/Component (B) (ratio by mass) | 2.5 | 2.5 | | | | | |
| | | Evaluation | | | | | | | |
| | | Brightness-I (Visual Observation) | B | A | C | B | C | C | B |
| | | Brightness-II (Glossy meter) | B | A | C | C | B | C | A |
| | | Color development (Color-meter) | B | A | B | A | C | C | B |
| | | rub resistance (Sensory) | A | B | B | C | B | B | A |
| | | Stability | A | A | A | A | A | A | B |
| | | Re-dispersibility | A | B | A | B | A | A | A |

※1 Product name: Cosmicolor Celeste Frost Silver (Toyo Aluminum K.K.) Silica coating amount 20 to 24%
※2 Product name: Cosmetic aluminum powder-CAL-1000 (Toyo AluminumK.K.) Aacrylic acid alkyl copolymer coating
※3 Product name: HELIOS R20S (Topy Industries Ltd.)
※4 Product name: CLOISSONE BLUE (Merck)
※5 Product name: METASHINE MC1020RS1 (Nippon Sheet Glass Co., Ltd.)
※6 Product name: JURYMER AC-103 (Toagosei Co., Ltd.) Solid content of 40%
※7 Product name: DAITOSOL 5000SJ(Daitokasei Kogyo K.K.) Solid content of 50%
※8 Product name: AQUADEW SPA-30B (Ajinomoto Co., Inc.) Solid content of 30%

As is apparent from the results shown in Table 1, the eye liners of Examples 1 to 2 were excellent in all evaluation items of brightness, color development, rub resistance, stability, and re-dispersibility. On the other hand, the eye liners of Comparative Examples 1 to 4 using titanium dioxide-coated synthetic mica, Prussian blue-coated (titanium dioxide-coated mica) or titanium dioxide-coated plate like glass any of which is a glittering powder instead of the component (A) were insufficient in brightness. Also, rub resistance was inferior compared to the eye liners of Examples 1 to 2. In addition, the eye liner containing an flaky aluminum powder having no silicon compound-containing layer was excellent in brightness, but significantly inferior in stability (see Comparative example 5).

Examples 3 to 6 and Comparative Examples 6 to 9

<Eyeliner>
An eyeliner of the formulation shown in Table 2 was prepared according to the following production procedure and evaluated by the methods described above for brightness, rub resistance, and re-dispersibility. The results are also shown in Table 2.
(Production Procedure)
(1) After dissolving components 3 to 7 and 14 to 17 shown in Table 2 in purified water of component 2, an interference pigment of component 1 and inorganic pigments of components 10 to 13 were added, and subsequently a resultant mixture was thoroughly stirred to prepare a water dispersion containing an interference pigment and inorganic pigments.
(2) Polymer emulsions of components 8 to 9 were added to the resulting water dispersion and mixed well to obtain an eye liner.

TABLE 2

| | | Component | Example 3 | Example 4 | Example 5 | Example 6 | Comparative Example 6 | Comparative Example 7 | Comparative Example 8 | Comparative Example 9 |
|---|---|---|---|---|---|---|---|---|---|---|
| 1 | (A) | Silicon compound containing layer-coated aluminum powder ※1 | 2.00 | 6.00 | 10.80 | 4.00 | 4.00 | 4.00 | 4.00 | 4.00 |

TABLE 2-continued

|  | Component | Example 3 | Example 4 | Example 5 | Example 6 | Comparative Example 6 | Comparative Example 7 | Comparative Example 8 | Comparative Example 9 |
|---|---|---|---|---|---|---|---|---|---|
| 2 | Purified water | Balance | Balance | Balance | Balance | Balance | Balance | Balance | Bala-nce |
| 3 | 1,2-Pentanediol | 3.00 | 3.00 | 3.00 | 3.00 | 3.00 | 3.00 | 3.00 | 3.00 |
| 4 | 1,3-Butylene glycol | 5.00 | 5.00 | 5.00 | 5.00 | 5.00 | 5.00 | 5.00 | 5.00 |
| 5 | Phenoxyethanol | 0.75 | 0.75 | 0.75 | 0.75 | 0.75 | 0.75 | 0.75 | 0.75 |
| 6 | Hydroxyethyl cellulose | 0.25 | 0.25 | 0.25 | 0.30 | 0.30 | 0.30 | 0.30 | 0.30 |
| 7 (B) | Soduim polyacrylate ※6 | 2.00 | 7.00 | 8.00 | 4.00 | | | | 4.00 |
| 8 (C) | (Acrylate/Ethylhexyl acrylate)copolymer ※7 | 25.00 | | | 25.00 | 25.00 | 25.00 | 25.00 | |
| 9 (C) | (Styrene/Acrylates) copolymer ※9 | | 20.00 | 20.00 | | | | | |
| 10 (D) | Prussian blue | 7.50 | | | | 7.50 | 7.50 | 7.50 | 7.50 |
| 11 (D) | Red iron oxide | | 2.70 | | | | | | |
| 12 (D) | Yellow iron oxide | | 4.50 | | | | | | |
| 13 (D) | Carbon black | | 0.50 | 1.20 | | | | | |
| 14 | Trilaureth-4 phosphate ※10 | | 0.02 | 0.05 | | | 0.80 | | |
| 15 | Beheneth-30 ※11 | | 0.06 | 0.15 | | | | 0.80 | |
| 16 | Sodium polyaspartate ※8 | 1.25 | 1.80 | | | 3.90 | 1.25 | 1.25 | 1.25 |
| 17 | aminomethylpropanol | Appropriate amount | Appropriate amount | Appropriate amount | Appropriate amount | Appropriate amount | Appropriate amount | Appropriate amount | Appropriate amount |
|  | Total | 100.00 | 100.00 | 100.00 | 100.00 | 100.00 | 100.00 | 101.00 | 100.00 |
|  | Component (A)/Component (B) (ratio by mass) | 2.5 | 2.1 | 3.4 | 2.5 | | | | |
|  | Evaluation | | | | | | | | |
|  | Brightness-I (Visual Observation) | B | B | A | A | B | B | B | B |
|  | rub resistance (Sensory) | A | A | B | B | B | B | B | D |
|  | Re-dispersibility | A | A | A | A | D | D | D | A |

※9 Product name: DAITOSOL 5000STY(Daitokasei Kogyo K.K.) Solid content of 50%
※10 Product name: NIKKOL TLP-4(Nikko Chemicals Co., Ltd)
※11 Product name: NIKKOL BB-30(Nikko Chemicals Co., Ltd)

As is apparent from the results of Table 2, the eye liners of Examples 3 to 6 were excellent in all evaluation items of brightness, rub resistance, and re-dispersibility. On the other hand, any eyeliner of Comparative examples 6 to 8 that does not contain the component (B) has significantly poor re-dispersibility and the eyeliner of Comparative example 9 that does not contain the component (C) had poor rub resistance.

INDUSTRIAL APPLICABILITY

The aqueous liquid cosmetic of the present invention exhibits excellent brightness, color development and rub resistance, and also exhibits excellent storage stability and re-dispersibility. Therefore, it is suitably used for eye makeup applications such as eyeliners, eyebrows, eye colors, and the like.

What is claimed is:

1. An aqueous liquid cosmetic, comprising:
   1 to 20% by mass of (A) a flaky aluminum powder coated with a silicon compound-containing layer,
   0.5 to 10% by mass of (B) a polyacrylic acid-based dispersant having a mass-average molecular weight of 10,000 or less, and
   1 to 40% by mass of (C) a film-forming polymer emulsion in terms of a solid content,
   wherein the flaky aluminum power is aluminum metal or an aluminum alloy.

2. The aqueous liquid cosmetic according to claim 1, wherein a ratio by mass of the component (A) to the component (B) [(A)/(B)] is 1/0.1 to 1/2.

3. The aqueous liquid cosmetic according to claim 1, further comprising (D) a color pigment.

4. The aqueous liquid cosmetic according to claim 1, the cosmetic is an eye makeup cosmetic.

5. The aqueous liquid cosmetic according to claim 1, wherein the flaky aluminum powder is aluminum.

6. The aqueous liquid cosmetic according to claim 1, wherein the flaky aluminum powder is an aluminum alloy.

7. The aqueous liquid cosmetic according to claim 6, wherein the aluminum alloy comprises aluminum and at least one metal selected from silicon, magnesium, manganese, copper, zinc, nickel, vanadium, lead, antimony, tin, cadmium, bismuth, titanium, chromium, and iron.

* * * * *